(12) United States Patent
Wagner

(10) Patent No.: US 10,441,297 B2
(45) Date of Patent: Oct. 15, 2019

(54) SOUNDER FOR SIZING BONE IMPLANT

(71) Applicant: Zimmer, Inc., Warsaw, IN (US)

(72) Inventor: Terry W. Wagner, Mishawaka, IN (US)

(73) Assignee: Zimmer, Inc., Warsaw, IN (US)

( * ) Notice: Subject to any disclaimer, the term of this patent is extended or adjusted under 35 U.S.C. 154(b) by 551 days.

(21) Appl. No.: 15/133,879

(22) Filed: Apr. 20, 2016

(65) Prior Publication Data
US 2016/0345983 A1 Dec. 1, 2016

Related U.S. Application Data

(60) Provisional application No. 62/168,181, filed on May 29, 2015.

(51) Int. Cl.
*A61B 17/16* (2006.01)
*A61B 90/00* (2016.01)

(52) U.S. Cl.
CPC ............ *A61B 17/164* (2013.01); *A61B 90/06* (2016.02); *A61B 17/1668* (2013.01); *A61B 17/1675* (2013.01); *A61B 17/1684* (2013.01); *A61B 2090/061* (2016.02)

(58) Field of Classification Search
CPC .. A61B 17/164; A61B 90/06; A61B 2090/061
See application file for complete search history.

(56) References Cited

U.S. PATENT DOCUMENTS

| | | | |
|---|---|---|---|
| 4,959,066 A | 9/1990 | Dunn et al. | |
| 5,342,366 A | 8/1994 | Whiteside et al. | |
| 5,573,537 A | 11/1996 | Rogozinski | |
| 5,863,295 A | 1/1999 | Averill et al. | |
| 6,120,509 A * | 9/2000 | Wheeler | A61B 17/155 606/87 |
| 6,261,034 B1 * | 7/2001 | Cselle | B23B 51/02 408/229 |
| 6,517,581 B2 | 2/2003 | Blamey | |
| 7,401,667 B2 * | 7/2008 | Duscha | B23B 51/02 175/323 |
| 7,618,444 B2 | 11/2009 | Shluzas | |
| 7,665,935 B1 * | 2/2010 | Garrick | B23B 35/005 408/227 |

(Continued)

*Primary Examiner* — David W Bates
(74) *Attorney, Agent, or Firm* — Schwegman Lundberg & Woessner, P.A.

(57) ABSTRACT

Methods and systems for installing an implant in an intramedullary canal are discussed. In an example, an intramedullary sounder tool has a sounder head including a plurality of teeth extending proximally from a distal tip towards a shank extending from the sounder head, each tooth comprising a distal cutting edge, a middle scraping edge, and a proximal cutting edge. The sounder head can be advanced into the intramedullary canal until the scraping edge engages cortical bone. If the scraping edge does not engage cortical bone, sounder tools having successively larger diameters can be advanced into the intramedullary canal until a scraping edge does engage the cortical wall, thereby avoiding cutting and damaging of the cortical bone. At such point, the width of the intramedullary canal and the implant used therein can be determined using markings on the shank that indicate the diameter of the sounder head.

17 Claims, 9 Drawing Sheets

(56) References Cited

U.S. PATENT DOCUMENTS

| | | | |
|---|---|---|---|
| 8,052,361 B2* | 11/2011 | Mir | B23B 51/02 |
| | | | 408/230 |
| 8,152,808 B2 | 4/2012 | Steiner et al. | |
| 8,734,067 B2* | 5/2014 | Saito | B23B 51/00 |
| | | | 408/224 |
| 9,180,531 B2* | 11/2015 | Nakahata | B23B 35/005 |
| 10,195,675 B2* | 2/2019 | George | B23B 51/02 |
| 2003/0185640 A1* | 10/2003 | Ito | B23B 51/02 |
| | | | 408/230 |
| 2005/0107802 A1* | 5/2005 | Vanasse | A61B 5/1076 |
| | | | 606/102 |
| 2005/0135887 A1* | 6/2005 | Borschert | B23B 51/02 |
| | | | 408/230 |
| 2005/0272004 A1 | 12/2005 | Desrosiers | |
| 2006/0029477 A1* | 2/2006 | Anjanappa | B23B 51/02 |
| | | | 408/230 |
| 2006/0269372 A1* | 11/2006 | Goshima | B23B 51/02 |
| | | | 408/230 |
| 2012/0076597 A1* | 3/2012 | Krenzer | B23B 51/02 |
| | | | 408/227 |
| 2012/0179161 A1 | 7/2012 | Rains et al. | |
| 2014/0128987 A1 | 5/2014 | Kelley | |
| 2015/0093205 A1* | 4/2015 | Krenzer | B23B 51/009 |
| | | | 408/1 R |
| 2015/0202413 A1* | 7/2015 | Lappin | A61B 17/8897 |
| | | | 600/585 |

* cited by examiner

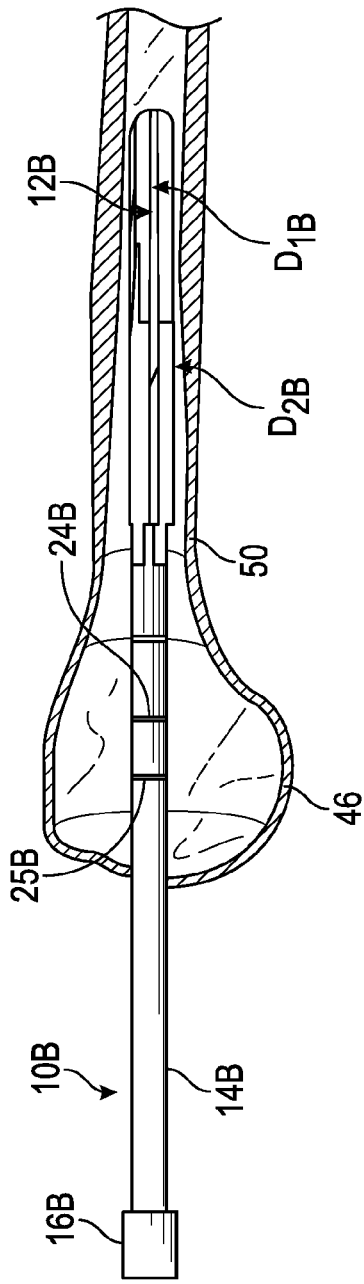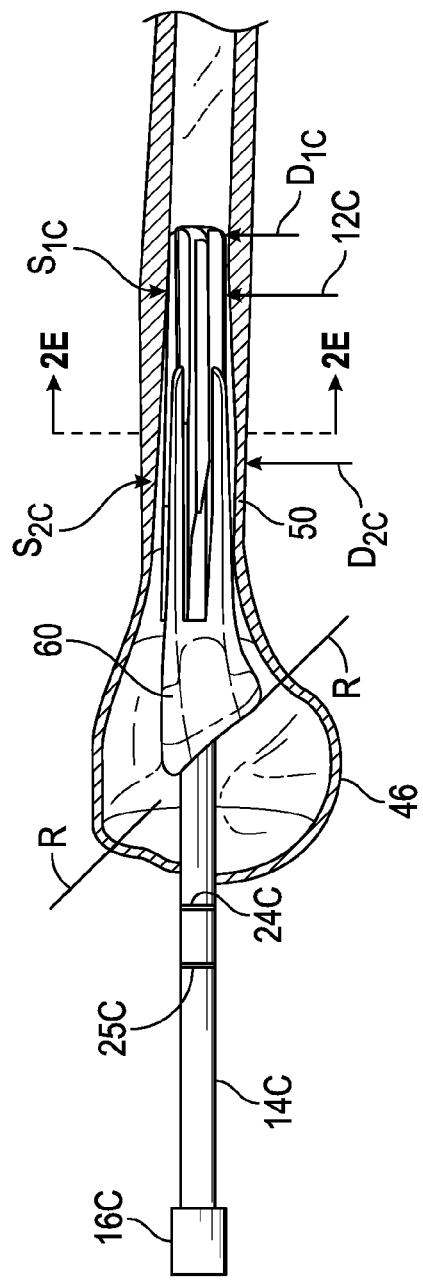

SOUNDER FOR SIZING BONE IMPLANT

CLAIM OF PRIORITY

This application claims the benefit of U.S. Provisional Patent Application Ser. No. 62/168,181, filed on May 29, 2015, the benefit of priority of which is claimed hereby, and which is incorporated by reference herein in its entirety.

FIELD

The present subject matter relates to orthopedic systems for arthroplasties, and specifically to tools used to implant a prosthesis within a medullary cavity of a long bone, such as a femur, tibia or humerus.

BACKGROUND

A natural joint may undergo degenerative changes due to a variety of etiologies. When these degenerative changes become so far advanced and irreversible, it may ultimately become desirable or necessary to replace the natural joint with a prosthetic joint. When implantation of such a joint prosthesis is implemented, the head of the natural bone, such as a femur, tibia or humerus, can be first resected and then a canal can be created within the medullary cavity of the host bone for accepting and supporting the prosthetic joint.

Because different patients have bones of various shapes, it is necessary to have available different appropriately structured prosthetic joint implants to accommodate these different shapes. Moreover, different patients having host bones with substantially the same sized medullary cavities may have differently shaped bone heads and necks, or vice versa. Consequently, a prosthetic joint assembly that has a diaphyseal portion that is appropriate for one host bone medullary cavity may not have an epiphyseal portion that is appropriate for the neck of the host bone. Thus, the most desirable fit may not always be possible, which can result in adverse effects on joint motion and patient comfort. Accordingly, it has become practice in the art to have prosthetic joint implants of different sizes, as described in U.S. Pat. No. 5,342,366 to Whiteside et al.

In order to determine which prosthetic joint implant to use with each patient, intraoperative procedures are sometimes used to measure various geometries of the host bone. It is particularly desirable to know the diameter of the stem at the diaphyseal portion of the prosthetic joint implant that will be implanted in the host bone and thus, the width to which to make the intramedullary canal. In preparing the medullary cavity for receiving the stem, it is desirable to remove some of the cancellous bone and/or make an implant shaped cavity within the cancellous bone from within the cortical bone in order to support the implant. As such, the implant will engage the cortical bone to facilitate osseointegration with the cortical bone wall. Additionally, it is desirable to not damage the cortical bone wall while reaming the bone canal because the cortical bone wall provides a substantial portion of the strength and rigidity of the host bone. Typically, doctors must remove the cancellous bone manually with a reamer, and a broach, as is described in U.S. Patent Application Pub. No. 2014/0128987 to Kelley and U.S. Pat. No. 6,517,581 to Blamey.

OVERVIEW

The present inventors have recognized, among other things, that problems to be solved with conventional arthroplasty tools can include determining the size to which to make the intramedullary canal without damaging the cortical bone wall. In an example, the subject matter described in this disclosure can provide a solution to this problem by providing an intramedullary sounder tool that has a sounder head including a plurality of teeth extending proximally from a distal tip towards a shank extending from the sounder head, each tooth comprising a distal cutting edge, a middle scraping edge, and a proximal cutting edge. The sounder head can be advanced into the intramedullary canal until the scraping edge engages cortical bone. If the scraping edge does not engage cortical bone, sounder tools having successively larger diameters can be advanced into the intramedullary canal until a scraping edge does engage the cortical wall at a desired depth where implant engagement would take place. As such, damaging of cortical bone with cutting teeth is avoided. At such point, the width of the intramedullary canal can be determined using markings on the shank that indicate the diameter of the size of a prosthetic implant, which corresponds to the diameter of the sounder head that scrapes the cortical wall.

To further illustrate the components and methods disclosed herein, a non-limiting list of examples is provided here:

In Example 1, a tool for performing an arthroplasty, the tool comprises: a shank extending along a central axis of the tool; and a sounder head comprising: a distal tip; a plurality of teeth extending proximally from the distal tip towards the shank, each tooth comprising: a distal cutting edge; a middle scraping edge; and a proximal cutting edge; and a proximal portion connected to the shank.

Example 2 can include, or can optionally be combined with the subject matter of Example 1, to optionally include a shank including graduation marks indicating sizes of the middle scraping edge.

Example 3 can include, or can optionally be combined with the subject matter of Examples 1 and 2, to optionally include each of the distal cutting edges having a first positive rake angle, each of the middle scraping edges having a negative rake angle, and each of the proximal cutting edges having a second positive rake angle.

Example 4 can include, or can optionally be combined with the subject matter of Example 3, to optionally include a second positive rake angle that is greater than the first positive rake angle.

Example 5 can include, or can optionally be combined with the subject matter of Examples 3 and 4, to optionally include each of the plurality of teeth including: a radial tooth surface having: a distal panel disposed at the first positive rake angle; an intermediate panel disposed at the negative rake angle; and a proximal panel disposed at the second positive rake angle.

Example 6 can include, or can optionally be combined with the subject matter of Example 5, to optionally include each of the plurality of teeth including: an outer tooth surface having: an arcuate distal segment; a tapered flat segment extending proximally from the arcuate distal segment; and a cylindrical flat segment extending proximally from the tapered flat segment.

Example 7 can include, or can optionally be combined with the subject matter of Example 6, to optionally include a distal panel that meets the arcuate distal segment to form the distal cutting edge; an intermediate panel that meets the tapered flat segment to form the scraping edge; and a proximal panel that meets the tapered flat segment to form the proximal cutting edge.

Example 8 can include, or can optionally be combined with the subject matter of Examples 1-7, to optionally include a sounder head including a taper from the proximal cutting edge to the distal cutting edge.

Example 9 can include, or can optionally be combined with the subject matter of Example 8, to optionally include a scraping edge that includes the taper.

Example 10 can include, or can optionally be combined with the subject matter of Examples 8 and 9, to optionally include a taper that is approximately 1.25 degrees relative to the central axis.

Example 11 can include, or can optionally be combined with the subject matter of Examples 1-10, to optionally include a proximal cutting edge having a larger diameter than the scraping edge and the distal cutting edge.

Example 12 can include, or can optionally be combined with the subject matter of Examples 1-11, to optionally include a sounder head further comprising a cylindrical section extending between the proximal portion and the proximal cutting edges.

In Example 13, a method for sizing an intramedullary canal of a bone comprises: advancing a first sounder tool having a first tapered diameter into a medullary cavity in the bone using a first distal cutting edge of a sounder head; and stopping advancement of the sounder tool if a first scraping edge of the sounder head engages cortical bone of the bone.

Example 14 can include, or can optionally be combined with the subject matter of Example 13, to optionally include advancing successive sounder tools having successively larger tapered diameters into the medullary cavity using successively larger distal cutting edges until a successive scraping edge engages cortical bone of the bone.

Example 15 can include, or can optionally be combined with the subject matter of Examples 13 and 14, to optionally include taking a diameter measurement of the intramedullary canal using a marking on a shank extending from the sounder head.

Example 16 can include, or can optionally be combined with the subject matter of Examples 13-15, to optionally include selecting a prosthetic implant having a size based on a diameter of the sounder head that scrapes cortical bone.

Example 17 can include, or can optionally be combined with the subject matter of Examples 14-16, to optionally include each of the sounder tools having a taper angle that is the same.

In Example 18, a tool set for performing an arthroplasty comprises: a first tool comprising: a first shank; and a first cutting head, the first cutting head comprising: a first distal tip; a plurality of edges extending proximally from the first distal tip towards the first shank, each edge comprising: a first distal cutting edge; a first middle scraping edge; and a first proximal cutting edge; and a second tool comprising: a second shank; and a second cutting head, the second cutting head comprising: a second distal tip; a plurality of edges extending proximally from the second distal tip towards the second shank, each cutting edge comprising: a second distal cutting edge; a second middle scraping edge; and a second proximal cutting edge; wherein a first diameter of the first cutting head is greater than a second diameter of the second cutting head.

In Example 19 can include, or can optionally be combined with the subject matter of Example 18, to optionally include a first shank including a graduation mark indicating the first diameter at a location on the first shank, and the second shank includes a graduation mark indication the second diameter at a location on the second shank.

Example 20 can include, or can optionally be combined with the subject matter of Examples 18 and 19, to optionally include a first implant having a diameter of the first cutting head; and a second implant having a diameter of the second cutting head.

These and other examples and features of the present systems and methods will be set forth in part in the following Detailed Description. This Overview is intended to provide non-limiting examples of the present subject matter—it is not intended to provide an exclusive or exhaustive explanation. The Detailed Description below is included to provide further information about the present systems and methods.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various examples discussed in the present document.

FIG. 2C is a diagrammatic view of a second sounder tool, larger than the first sounder tool, inserted to widen the tapered intramedullary canal of FIG. 2B.

FIG. 2D is a diagrammatic view of the third sounder tool, larger than the second sounder tool, inserted into the intramedullary canal to match a size of the joint replacement implant.

DETAILED DESCRIPTION

Example systems and methods for producing an intramedullary canal and simultaneously determining a size of an implant for that intramedullary canal are described. A set of intramedullary canal sounders can be used to determine the intramedullary canal size and the corresponding implant size during an intraoperative procedure. Each sounder can have a sounder head having a non-cutting, scraping edge that inhibits advancement of a distal tip cutting edge, thereby preserving cortical bone. Successively larger diameter sounder heads can be advanced into the intramedullary canal until the non-cutting, scraping edge engages the cortical bone. An implant can be selected based on a diameter of the sounder head at selected positions along the scraping edge.

Figure 1:
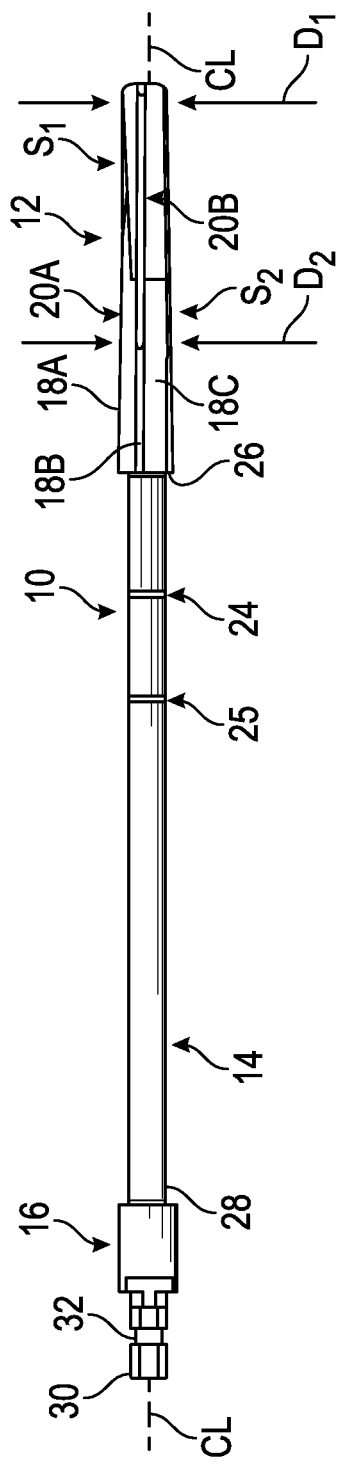
FIG. 1 is a side view of a sounder tool having a sounder head and a shank that are used in producing an intramedullary canal during arthroplasty, i.e. a joint replacement procedure.
Figure 3:
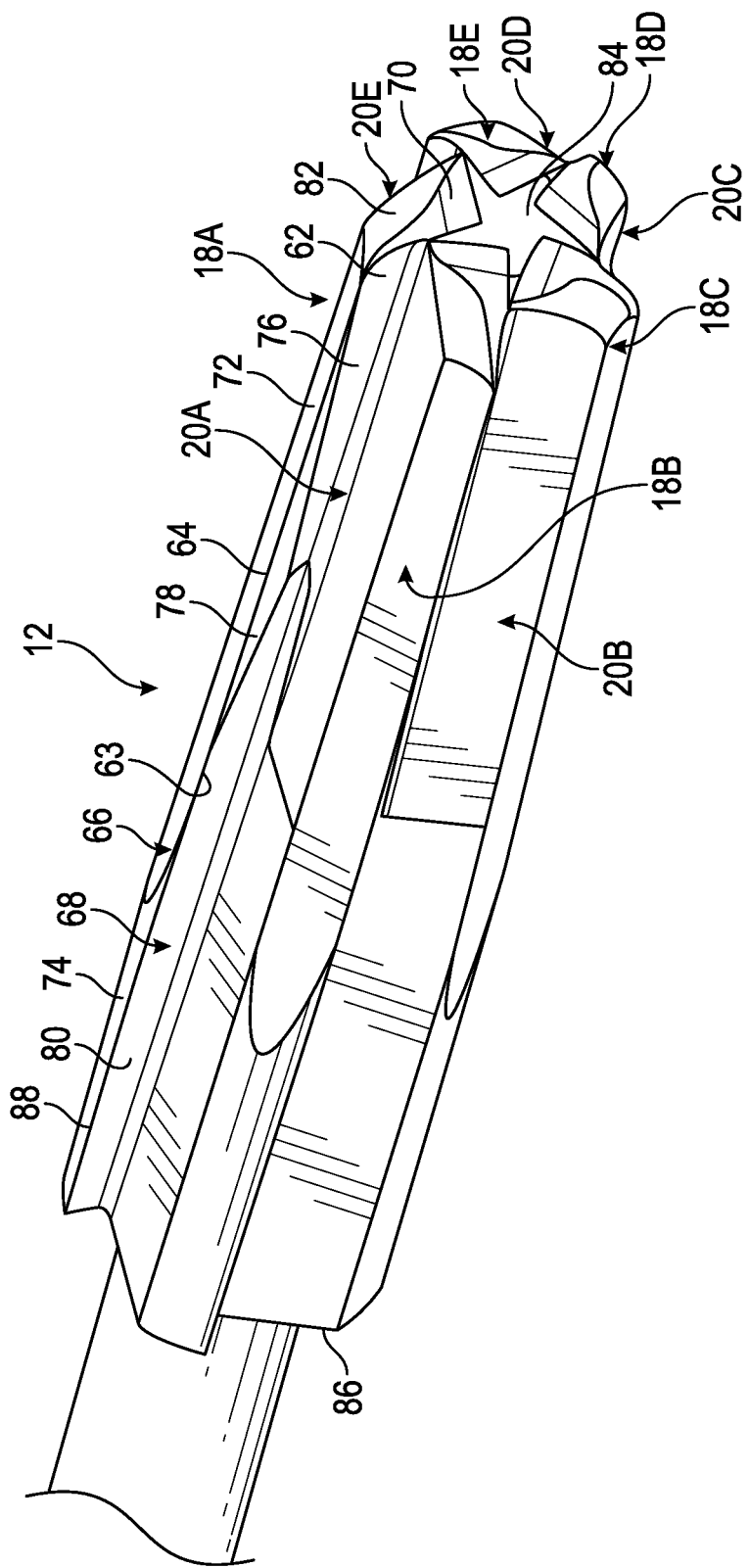
FIG. 3 is a perspective view of the sounder head of FIG. 1 showing proximal and distal cutting edges and an intermediate scraping edge of a tooth.

Referring to the drawings, FIG. 1 is a side view of sounder tool 10 having sounder head 12 and shank 14 that are used in producing an intramedullary canal during arthroplasty, i.e. a joint replacement procedure. Shank 14 can connect sounder head 12 to connector 16, each of which can extend co-axially along center line CL. Sounder head 12 can include teeth 18A, 18B and 18C, as well as teeth 18D and 18E (FIG. 3), between which can be formed flutes 20A and 20B, as well as flutes 20C, 20D and 20E (FIG. 3). Shank 14 can include graduation marks 24 and 25, distal end 26 and proximal end 28.

Proximal end 28 of shank 14 can include connector 16, which can include tool-receiving portion 30 and annular recess 32. Connector 16 can be configured as a Hall shank, which includes hexagonal receiving portion 30 having circumscribing annular recess 32. Such Hall shanks are additionally described in U.S. Pat. No. 7,618,444 to Shluzas. Tool-receiving portion 30 and annular recess 32 of connector 16 can be configured for locking shank 14 to a drive tool, such as a T-handle 44 of FIG. 2A. Shank 14 can be cylindrical and have a smaller diameter than sounder head 12, or can be equal or greater in diameter. Graduation marks 24 and 25 can be disposed on shank 14 a known or pre-determined distance from sounder head 12 and provide an indication of the diameter of sounder head 12, which corresponds to the size of an implant that can be implanted after using sounder head 12.

Teeth 18A-18E of sounder head 12 can be used to widen an intramedullary canal through a bone by removing cancellous bone from within the bone. Teeth 18A-18E can be tapered from a second cutting edge 63 (FIG. 3) at second diameter $D_2$ to a first cutting edge 62 (FIG. 3) at a smaller first diameter $D_1$. Between diameters $D_1$ and $D_2$, teeth 18A-18E can include a non-cutting, scraping edge 64 (FIG. 3) that is prevented from removing material from the cortical wall and inhibits further axial advancement of sounder tool 10 into the bone. Sizing locations $S_1$ and $S_2$ can be selected between diameters $D_1$ and $D_2$ along scraping edge 64 (FIG. 3) to determine the sizes of implants that can be used with the canal formed by sounder head 12.

It is known in the art that the cortical wall of a long bone is generally tapered from a larger diameter near the head to a smaller diameter further down the shaft of the bone. One study has found that the taper angle is approximately 1.25 degrees per size. However, long bones can have a variety of different diameters such that the diameters of the cortical wall can vary, even though it tapers at the same rate. Thus, it can be desirable to provide implants that match both the taper and diameter of the cortical wall.

Sounder head 12 can comprise one of a set of sounder heads that have increasingly larger diameters to accommodate joint replacement implants of increasing size. Sounder head 12, and each of the sounder heads of the set, can include distal cutting edge 62 (FIG. 3) that allows the sounder head to advance into the cancellous bone, non-cutting, scraping edge 64 (FIG. 3) that inhibits advancement of the sounder head into cortical bone, and proximal cutting edge 63 (FIG. 3) that clears the way for the introduction of the next larger sounder head. As discussed below with reference to FIG. 8, the size of the sounder head that engages the cortical bone can be used to determine the size of joint replacement implant 60 (FIG. 2D).

Figure 2A:
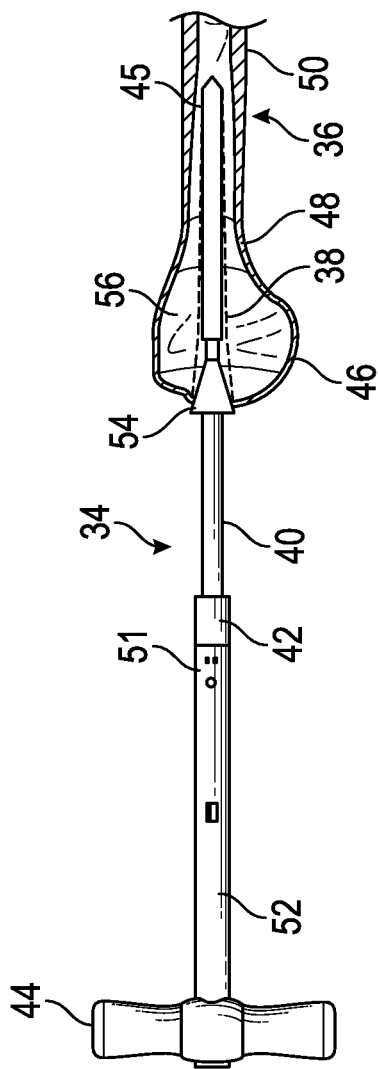
FIG. 2A is a diagrammatic view of a starter awl being inserted into a medullary cavity of a long bone to form an intramedullary canal.

FIG. 2A is a diagrammatic view of starter awl 34 being inserted into long bone 36 to form intramedullary canal 38. Shaft 40 of starter awl 34 can include coupler 42 for connecting to T-handle 44. Shaft 40 can also include twist reamer 45 that can be used to form intramedullary canal 38 in the medullary cavity of bone 36. Bone 36 can include head 46, neck 48 and shaft 50. Coupler 42 can be configured to connect to coupler 51 on shaft 52 of T-handle 44. Coupler 42 can be configured as a Hall shank that has a hexagonal receiving portion with a circumscribing annular recess, while coupler 51 can have a mating hexagonal socket with a detent that engages the annular recess. Shaft 40 of awl 34 can be driven into long bone 36 via pressure asserted against T-handle 44 (as shown) or other suitable manual or power-inserting instrument. Twist reamer 45 can be inserted until trephine 54 impacts head 46. T-handle 44 can be manually rotated to drive twist reamer 45 into cancellous bone 56 of long bone 36 to form intramedullary canal 38, which serves as an initial passage through cancellous bone 56 for introducing other tools. Trephine 54 can produce a funnel-shaped introductory passage in canal 38 to facilitate receiving other tools into canal 38. In one example, twist reamer 45 can be configured to produce an 8 mm starter canal. Canal 38 can then serve as a guide canal for receiving sounder tool 10 of FIG. 1.

Figure 2B:
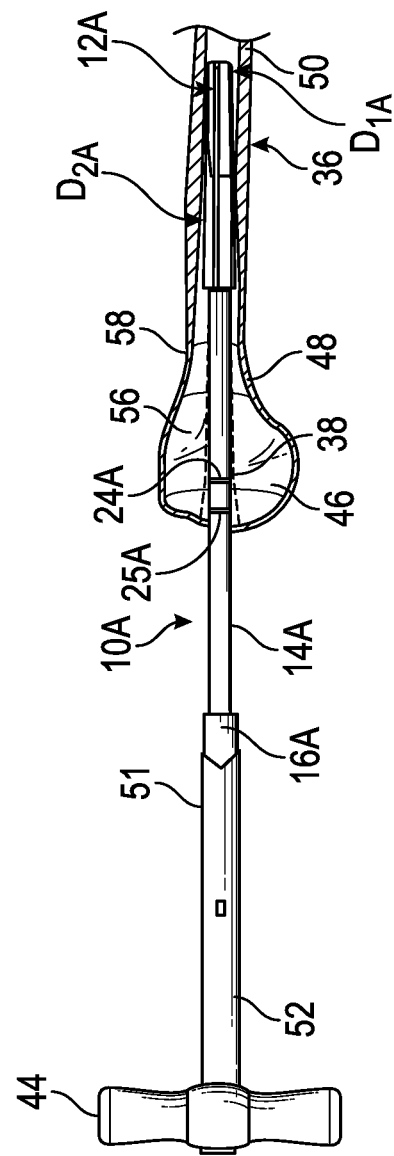
FIG. 2B is a diagrammatic view of a first sounder tool, such as the tool of FIG. 1, being inserted into the long bone of FIG. 2A to taper the intramedullary canal in preparation for receiving a joint replacement implant.

FIG. 2B is a diagrammatic view of sounder head 12A, similar to sounder head 12 of FIG. 1, being inserted into long bone 36 of FIG. 2A to taper intramedullary canal 38 in preparation for receiving joint replacement implant 60 (FIG. 2D). Sounder tool 10A can be used to remove cancellous bone 56 from the interior of cortical bone 58 in head 46, neck 48 and shaft 50 of bone 36. Connector 16A of shank 14A can be, for example, connected to coupler 51 on shank 52 of T-handle 44 via tool-receiving portion 30 and annular recess 32 (FIG. 1). In one example, tool-receiving portion 30 and annular recess 32 can form a Hall shank. Sounder head 12A can remove cancellous bone 56 while minimizing damaging or weakening of cortical bone 58. Sounder head 12A can include diameters $D_{1A}$ and $D_{2A}$ that correspond to the smallest sizes of implant 60. Cutting edge 62 (FIG. 3) at diameter $D_{1A}$ can widen canal 38 to clear the way for the scraping edge. Scraping edge 64 (FIG. 3) can be capable of removing cancellous bone 56, but not cortical bone 58. Cutting edge 63 (FIG. 3) at diameter $D_{2A}$ can widen canal 38 beyond what is done by the cutting edge at diameter $D_{1A}$. As long as teeth of sounder head 12A continue to cut cancellous bone 56, sounder tool 10A can be advanced into canal 38 until gradation marks 24A and 25A are recessed into canal 38. This can indicate that the non-cutting scraping edge 64 (FIG. 3) of sounder head 12A did not engage cortical bone 58. This also indicates that a larger diameter sounder head, and implant, can be needed.

FIG. 2C is a diagrammatic view of second sounder tool 10B, larger than first sounder tool 10A of FIG. 2B, inserted to widen tapered intramedullary canal 38. Sounder head 12B can be slightly larger than sounder head 12A such that diameters $D_{1B}$ and $D_{2B}$ are larger than diameters $D_{1A}$ and $D_{2A}$. Specifically, diameter $D_{1B}$ can be larger than diameters $D_{1A}$ and $D_{2A}$, and diameter $D_{2B}$ can be larger than diameter $D_{1B}$. The diameters can incrementally increase in size between successively larger sounder heads so as to avoid damage of cortical bone 58. A sounder head having approximately the same distal tip diameter as the wall formed by cortical bone 58 can only cut at the smaller tip diameter ($D_{1A}$, $D_{1B}$, etc.), not at the proximal diameter ($D_{2A}$, $D_{2B}$), and will scrape against cortical bone 58 at scraping edge 64 (FIG. 3). As shown in FIG. 2C, sounder head 12B is too small for cortical bone 58 as cutting has continued at the cutting edge of proximal diameter $D_{2B}$ and scrapping edge 64 (FIG. 3) between diameters $D_{2A}$ and $D_{2B}$ has not engaged cortical bone 58. As a result graduation marks 24B and 25B have receded into canal 38, indicating a larger sounder head can be needed.

FIG. 2D is a diagrammatic view of third sounder tool 10C, larger than second sounder tool 10B of FIG. 2C, inserted into intramedullary canal 38 to match a size of joint replacement implant 60. Joint replacement implant 60 is diagrammatically shown in FIG. 2D overlaying sounder head 12C in order to provide a size comparison. However, in practice, implant 60 would not be installed until after sounder tool 10C is removed from intramedullary canal 38. Distal diameter $D_{1C}$ of sounder head 12C can be in close proximity to cortical bone 58, while proximal diameter $D_{2C}$ can be slightly spaced from cortical bone 58. As such, scraping edge 64 (FIG. 3) between diameters $D_{1C}$ and $D_{2C}$ scrapes against cortical bone 58, preventing further advancement of sounder head 12C into canal 38. At such point, one or both of graduation marks 24C and 25C will not have entered into canal 38. Thus, a surgeon can determine the size of an implant that should be used in canal 38 by determining which graduation mark is closest to cortical bone 58 where shank 14C enters head 46. In the illustrated example, graduation mark 24C is proximate cortical bone 58. Thus, an implant having the size indicated by graduation mark 24C can be used. However, a surgeon may wish to use an implant of a different size based on other factors. In any event, sounder tool 10C can provide an indication of the range of implants that can be used without damaging cortical bone 58. Intramedullary canal 38 can thus be formed by sounder head 12C within cancellous bone 56 in close proximity to cortical bone 58.

Sounder head 12C and implant 60 can have approximately the same outer diameters. This can allow implant 60 to closely engage cortical bone 58 to facilitate bone growth and osseointegration. Head 44 can be resected along line R-R at neck 46 to generate a surface that extends across canal 38. Removal of bone along line R-R can allow another component, such as a glenosphere or baseplate, to be mounted to implant 60.

Figure 2E:
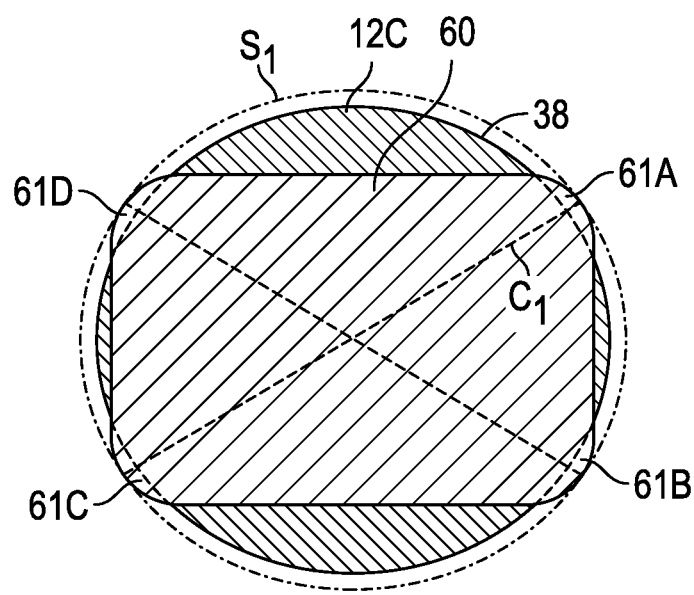
FIG. 2E is a cross-sectional view of the sounder head of FIG. 2D showing the relative size of the joint replacement implant at a sizing location.

FIG. 2E is a cross-sectional view of sounder head 12C of FIG. 2D showing the relative size of joint replacement implant 60 at a sizing location $S_2$ on sounder head 12C within intramedullary canal 38 (FIG. 2A). Joint replacement implants having rectangular cross-section that the sounders were designed for can typically be sized by their diagonal corner to corner distance $C_1$. Joint replacement implants can typically be sized in one millimeter increments, such as 7 mm up to 16 mm. Sizing location $S_2$ can be determined at a location along scraping edge 64 of sounder head 12C that is 1 mm smaller that the corresponding implant size in order to produce the desired interface between cortical bone 58 and implant 60. Thus, in the example of FIG. 2E, sizing location $S_2$ can be approximately 15 mm and distance $C_1$ can be approximately 16 mm. In one example, a rasp or broach can be used to make corner cuts 61A-61D in canal 38 approximately 0.5 mm deep to stabilize implant 60. In other examples, the sounder tools described herein can be used with implants of other shapes, such as those have square, circular or elliptical cross-sections among others. In yet other examples, the sizing locations can correspond to the same size as the implant such that it is unnecessary to make corner cuts 61A-61D. In other words, sounder head 12 can be used to make a canal of a known size for use with any implant that will seat well within such a sized canal.

Due to the taper angle α of sounder head 12C being 1.25 in the described example, sizing location $S_1$ can be located approximately 23 mm distally from sizing location $S_2$. For such a taper angle, it is necessary to traverse an axial distance of 23 mm for the sounder head to change 1 mm in diameter. For the example of FIGS. 2D and 2E, sizing location $S_1$ would have a 14 mm diameter corresponding to an implant size of 15 mm. Thus, the distance between sizing locations, and the distance between graduation marks 24 and 25, can be located a different distance apart based on the selected taper angle α.

Graduation marks 24 and 25 can be located 23 mm apart on shank 14 (FIG. 1). The graduation marks on each sounder tool can be located 23 mm apart and indicate implant sizes 1 mm in difference, with the distal graduation mark 24 indicating an implant size 1 mm smaller than the proximal graduation mark 25.

FIG. 3 is a perspective view of sounder head 12 of FIG. 1 showing tooth 18A having distal and proximal cutting edges 62 and 63, and intermediate scraping edge 64. Sounder head 12 can also include teeth 18B-18E. Flutes 20A-20E can be formed between teeth 18A-18E. Tooth 18A can include outer tooth surface 66 and radial tooth surface 68. Outer tooth surface 66 can include arcuate distal segment 70, tapered segment 72 and cylindrical segment 74. Radial tooth surfaced 68 can include distal panel 76, intermediate panel 78 and proximal panel 80. Tooth 18A can also include chamfer 82. Sounder head 12 can include distal tip 84 and proximal portion 86.

Each of teeth 18A-18E can include features as is described with reference to tooth 18A, but labeling and discussion of such features is omitted for brevity and clarity of FIG. 3. The configuration of teeth 18A-18E results in sounder head 12 having flutes 20A-20E. Teeth 18A-18E and flutes 20A-20E can cooperate to remove bone material from intramedullary canal 38 (FIGS. 2A-2D) when sounder head 12 is inserted therein and rotated.

Distal tip 84 can comprise a relief feature that can allow distal cutting edge 62 to cut bone material. Chamfer 82 can comprise a panel that flattens out sounder head 12 between arcuate distal segment 70 and tapered segment 72 in order to eliminate a sharp edge therebetween. Arcuate distal segment 70 forms distal cutting edge 62 along the interface with distal panel 76.

Scraping edge 64 can extend from the intersection of cutting edge 62, tapered segment 72 and distal panel 76 to the intersection of tapered segment 72, proximal panel 80 and intermediate panel 78. Intermediate panel 78 can be positioned radially between tapered segment 72 and the junction of distal panel 76 and proximal panel 80. As such, intermediate panel 78 can have a triangular shape. Scraping edge 64 can be formed along the junction of intermediate panel 78 and tapered segment 72. Intermediate panel 78 extends in a plane that is parallel to center line CL. Intermediate panel 78 is formed in material of sounder head 12 that results from distal panel 76 and proximal panel 80 being angled relative to center line CL. The point where distal panel 76, proximal panel 80 and intermediate panel 78 come together is advanced forward in the direction that sounder head 12 is rotated to produce cutting relative to the locations of cutting edges 62 and 63. Distal panel 76 converges toward center line CL from the edge of contact with proximal panel 78 in the distal direction. Proximal panel 78 converges toward center line CL from the edge of contact with distal panel 76 in the proximal direction. From the juncture with distal panel 76 and proximal panel 80, intermediate panel 78 is angled back toward center line CL in order to form scraping edge 64 generally in line with cutting edges 62 and 63. This configuration of intermediate panel 78, distal panel 76 and proximal panel 80 allows sounder head 12 to have the configuration of two different cutting edges and a scraping edge.

Proximal cutting edge 63 can extend from the intersection of tapered segment 72, intermediate panel 78 and proximal panel 80 to the intersection of tapered segment 72, proximal panel 80 and cylindrical segment 74.

Blunt edge 88 can extend from the intersection of tapered segment 72, proximal panel 80 and cylindrical segment 74 to proximal portion 86. Blunt edge 88 can be positioned between cylindrical segment 74 and proximal panel 80.

Figure 4:
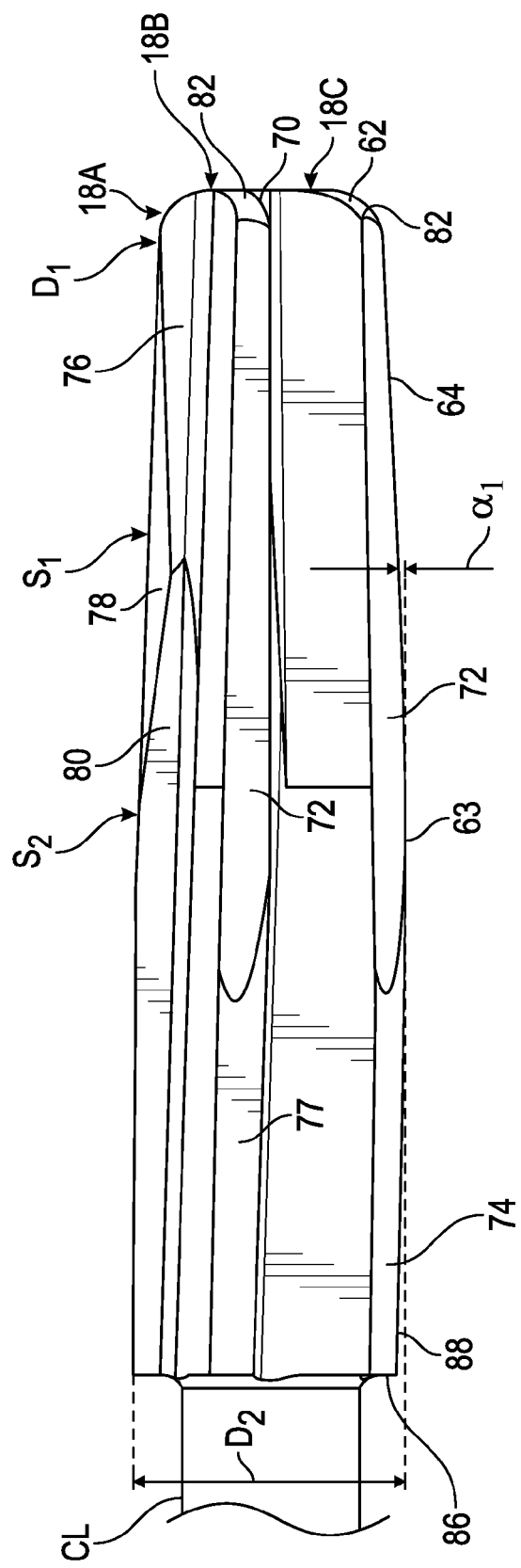
FIG. 4 is a side view of the sounder head of FIG. 3 showing a taper angle of the tooth of the sounder head.

FIG. 4 is a side view of sounder head 12 of FIG. 3 showing taper angle α of tooth 18C of sounder head 12. Sounder head 12 can also include teeth 18A and 18B. Tooth 18C can include chamfer 82, tapered segment 72 and cylindrical segment 74 that can cooperate to form distal cutting edge 62, scraping edge 64, proximal cutting edge 63 and blunt edge 88.

Distal cutting edge 62 can have diameter $D_1$ and proximal cutting edge 63 can have diameter $D_2$. Cylindrical segment 74 can extend linearly between cutting edge 63 and proximal portion 86 so as to also have diameter $D_2$. Diameter $D_1$ can be smaller than diameter $D_2$ so that tapered segment 72 has a taper angle. As explained with reference to FIG. 8, in the various sizes of sounder head 12, diameter $D_1$ can be smaller than a first size for implant 60 (FIG. 2D) that can correspond to first graduation mark 24 (FIG. 1) and the diameter at first sizing location $S_1$ (FIG. 1), and diameter $D_2$ can be larger than a second size for implant 60 (FIG. 2D) that can correspond to second graduation mark 25 (FIG. 1) and the diameter at second sizing location $S_2$ (FIG. 1). As can be seen in FIG. 4, tapered segment 72 can extend linearly between proximal cutting edge 63 and distal cutting edge 62, at an angle to cylindrical segment 74, which is parallel to center line CL. In one example, taper angle α can be approximately 1.25 degrees. In total, sounder head 12 can be tapered approximately 2.5 degrees including taper from both sides. Studies have shown that such an angle is representative of typical medullary cavities in long bones. However, in other examples, taper angle α may form other angles between tapered segment 72 and cylindrical segment 74. For example, taper angle α may be in the range of about 0.5 degrees to about 2.0 degrees to encompass the majority of medullary cavities in bones of all types.

Configured as such, sounder head 12 can engage cortical bone 58 (FIG. 2B) at scraping edge 64. First, distal cutting edge 62 can engage cancellous bone 56 (FIG. 2B) and cut a path therethrough. If the distal portion of scraping edge 64 engages cortical bone 58, that can be an indication that the size indicated by graduation mark 24 (FIG. 1) can be used for implant 60. If the proximal portion of scraping edge 64 engages cortical bone 58, that can be an indication that the size indicated by graduation mark 25 (FIG. 1) can be used for implant 60. If scraping edge 64 does not engage cancellous bone, a larger sounder head 12 can be used to determine the size of implant 60.

Figure 5:
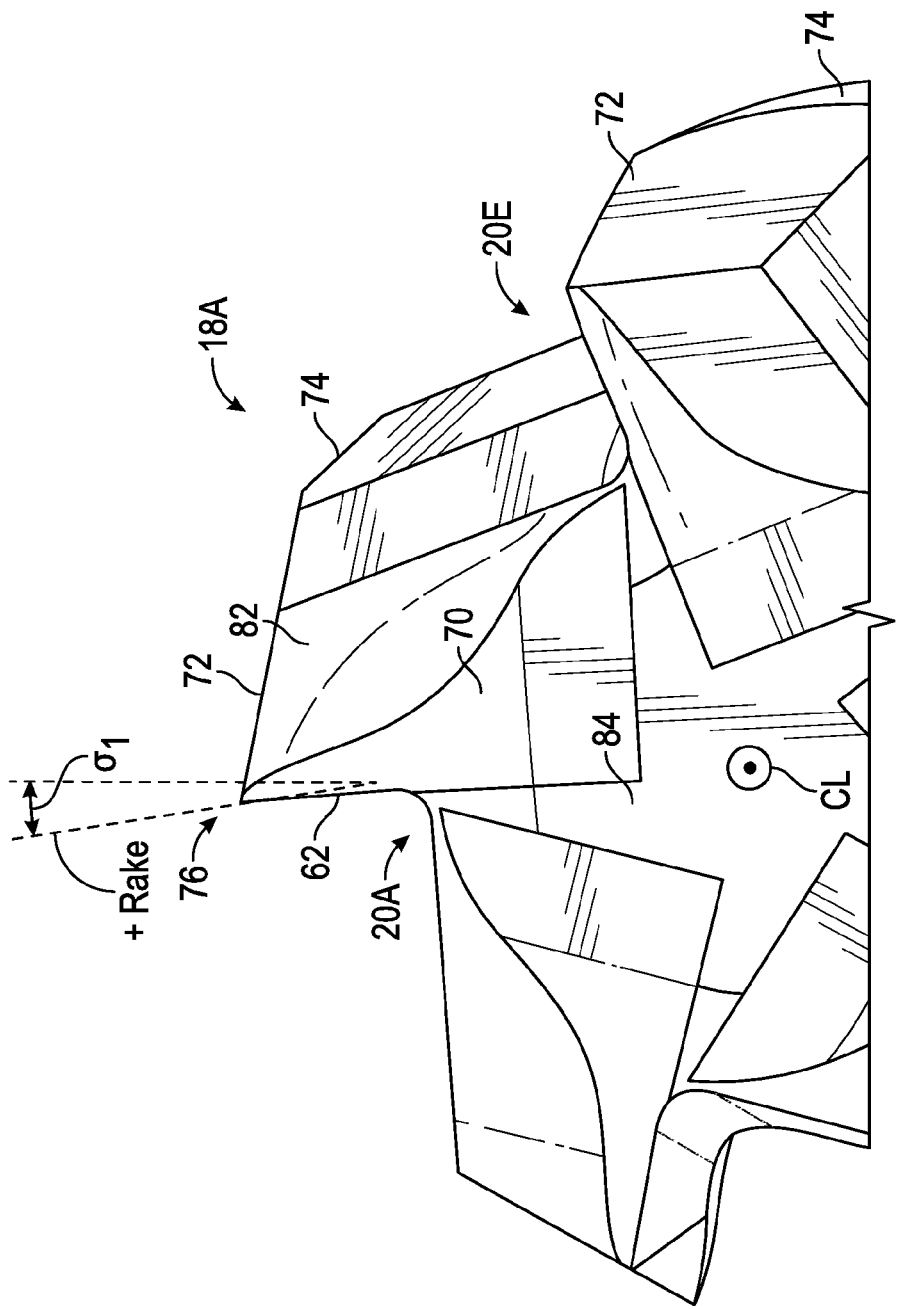
FIG. 5 is a perspective view of the distal end of the sounder head of FIG. 3 showing a positive rake angle for the distal cutting edge.

FIG. 5 is a perspective view of the distal end of sounder head 12 of FIG. 3 showing positive rake angle $\sigma_1$ for distal cutting edge 62. FIG. 5 is a view of sounder head 12 looking straight down distal panel 76, i.e., distal panel 76 is perpendicular to the plane of FIG. 5. Tapered segment 72 can be flat, and cylindrical panel 74 can be arcuate. In one example, rake angle $\sigma_1$ can be approximately 10 degrees. However, in other examples, rake angle $\sigma_1$ can be in the range of about 5 degrees to about 15 degrees. Rake angle $\sigma_1$ can be positive, meaning that cutting edge 62 is angled from vertical in the counter-clockwise direction with reference to FIG. 5, which is the direction that sounder head is rotated to cut bone. Arcuate distal segment 70 can provide a relief surface for cutting edge 62.

Figure 6:
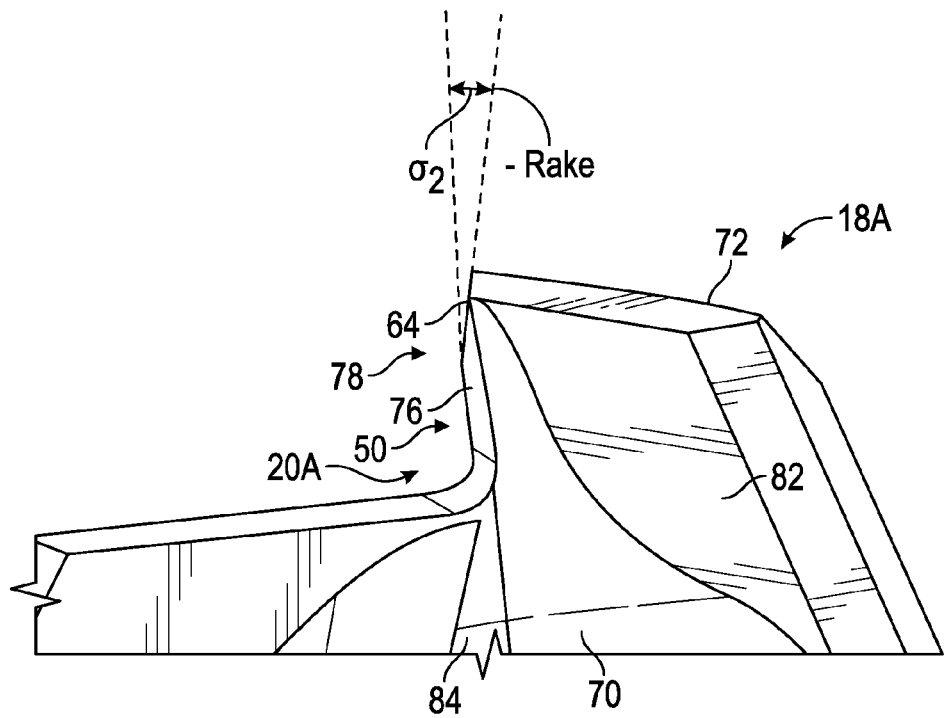
FIG. 6 is a perspective view of the distal end of the sounder head of FIG. 3 showing a negative rake angle of the intermediate scraping edge.

FIG. 6 is a perspective view of the distal end of sounder head 12 of FIG. 3 showing negative rake angle $\sigma_2$ of intermediate scraping edge 64. FIG. 6 is a view of sounder head 12 looking straight down intermediate panel 78, i.e., intermediate panel 78 is perpendicular to the plane of FIG. 6. In one example, rake angle $\sigma_2$ can be approximately 6 degrees. However, in other examples, rake angle $\sigma_2$ can be in the range of about 3 degree to about 9 degrees. Rake angle $\sigma_2$ can be negative, meaning that scraping edge 64 is angled from vertical in the clockwise direction with reference to FIG. 6, which is opposite the direction that sounder head is rotated to cut bone.

Figure 7:
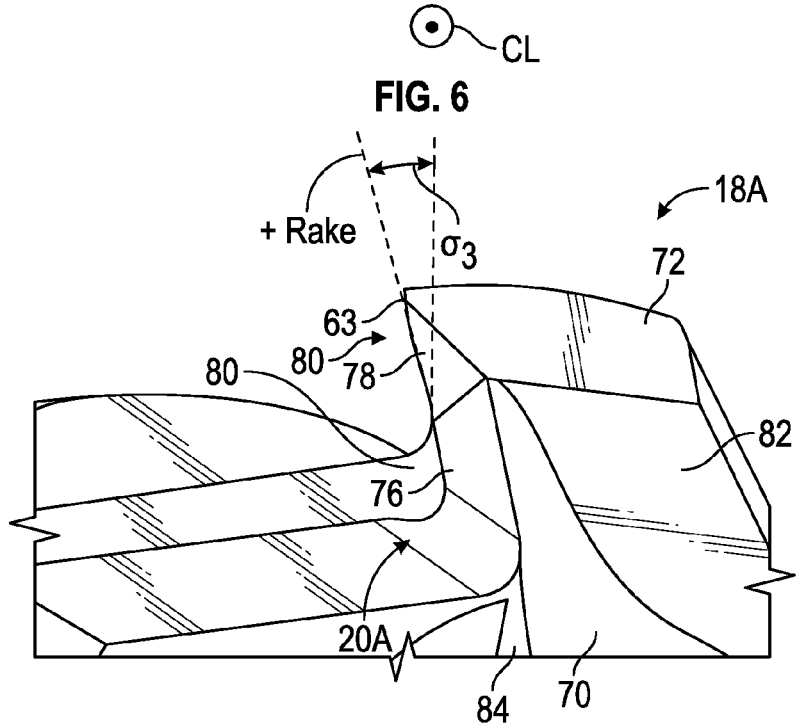
FIG. 7 is a perspective view of the distal end of the sounder head of FIG. 3 showing a positive rake angle of the proximal cutting edge.

FIG. 7 is a perspective view of the distal end of sounder head 12 of FIG. 3 showing positive rake angle $\sigma_3$ of proximal cutting edge 63. FIG. 7 is a view of sounder head 12 looking straight down proximal panel 80, i.e., proximal panel 80 is perpendicular to the plane of FIG. 7. In one example, rake angle $\sigma_3$ can be approximately 15 degrees. However, in other examples, rake angle $\sigma_3$ can be in the range of about 10 degrees to about 5 degrees. Rake angle $\sigma_3$ can be positive, meaning that cutting edge 63 is angled from vertical in the counter-clockwise direction with reference to FIG. 7, which is the direction that sounder head is rotated to cut bone. Tapered segment 72 can provide a relief surface for cutting edge 63. Although FIGS. 5-7 show rake angles $\sigma_1$, $\sigma_2$ and $\sigma_3$ being positive, negative and positive, respectively, rake angles $\sigma_1$, $\sigma_2$ and $\sigma_3$ can be arranged in other combinations, such as positive, positive, negative.

Figure 8:
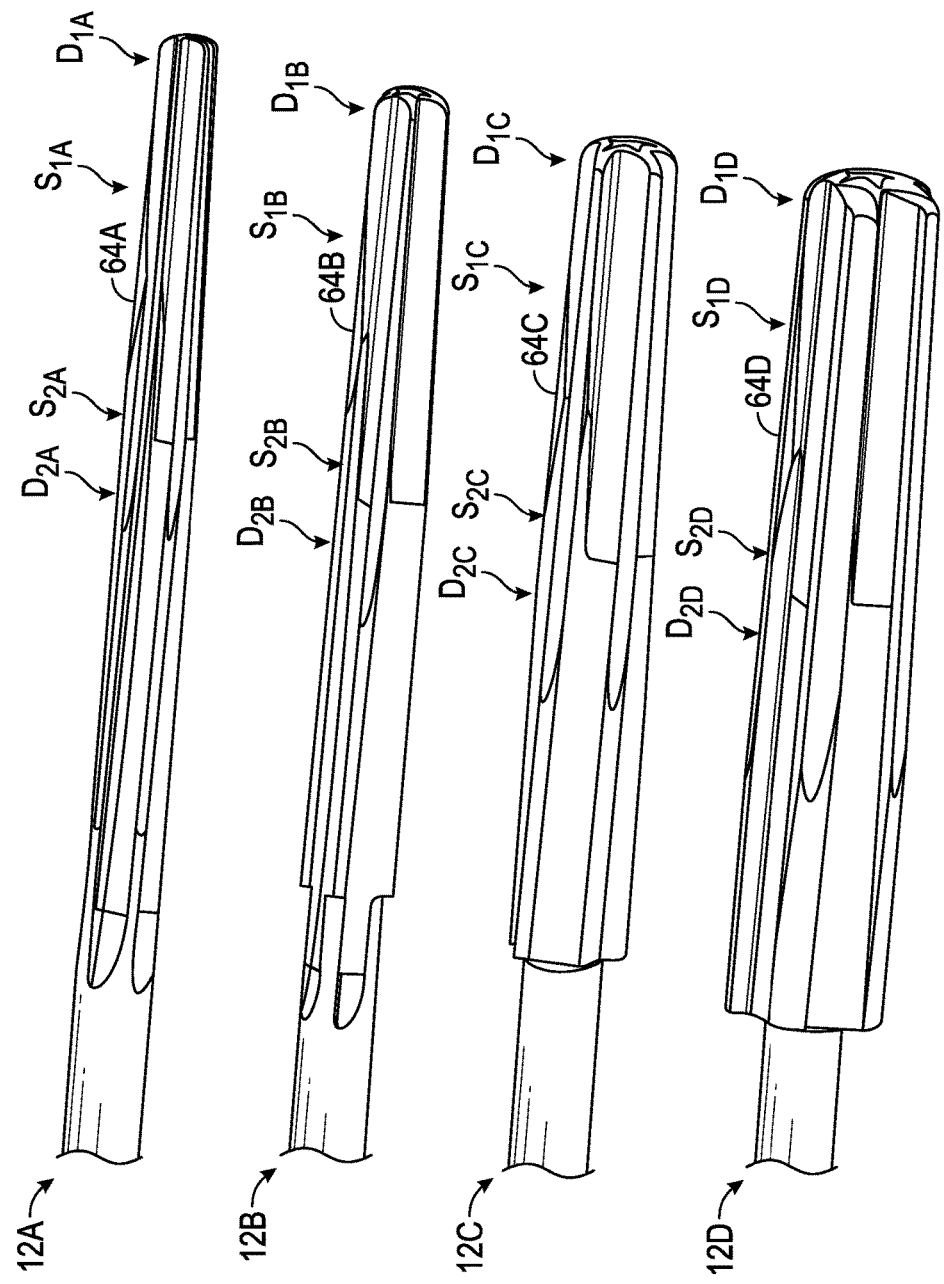
FIG. 8 is a perspective view of a set of sounder heads having successively larger diameters along their respective scraping edges.

FIG. 8 is a perspective view of set 90 of sounder heads 12A-12D having successively larger diameters along their respective scraping edges 64A-64D. Sounder head 12A of FIG. 2B can include scraping edge 64A between diameters $D_{1A}$ and $D_{2A}$. Sounder head 12B of FIG. 2C can include scraping edge 64B between diameters $D_{1B}$ and $D_{2B}$. Sounder head 12C of FIG. 2D can include scraping edge 64C between diameters $D_{1C}$ and $D_{2C}$. Sounder head 12D can include scraping edge 64D between diameters $D_{1D}$ and $D_{2D}$. As discussed with reference to FIG. 2E, sizing locations $S_1$ and $S_2$ can correspond to the diameter of sounder head 12 at such locations, which are slightly smaller than the size of an implant desirable for use at a canal of those sizes.

Sizing locations $S_{1A}$ and $S_{2A}$ can be located along scraping edge 64A between diameters $D_{1A}$ and $D_{2A}$. In one example of sounder head 12A, sizing location $S_{1A}$ can be approximately 6 mm and sizing location $S_{2A}$ can be approximately 7 mm, which can correspond to implant sizes of 7 mm and 8 mm, respectively, which can be marked by graduation marks 24 and 25 (FIG. 1), respectively.

Sizing locations $S_{1B}$ and $S_{2B}$ can be located along scraping edge 64B between diameters $D_{1B}$ and $D_{2B}$. In one example of sounder head 12B, sizing location $S_{1B}$ can be approximately 8 mm and sizing location $S_{2A}$ can be approximately 9 mm, which can correspond to implant sizes of 9 mm and 10 mm, respectively, which can be marked by graduation marks 24 and 25 (FIG. 1), respectively.

Sizing locations $S_{1C}$ and $S_{C2}$ can be located along scraping edge 64C between diameters $D_{1C}$ and $D_{2C}$. In one example of sounder head 12C, sizing location $S_{1C}$ can be approximately 10 mm and sizing location $S_{2C}$ can be approximately 11 mm, which can correspond to implant sizes of 11 mm and 12 mm, respectively, which can be marked by graduation marks 24 and 25 (FIG. 1), respectively.

Sizing locations $S_{1D}$ and $S_{2D}$ can be located along scraping edge 64D between diameters $D_{1D}$ and $D_{2D}$. In one example of sounder head 12D, sizing location $S_{1D}$ can be approximately 14 mm and sizing location $S_{2D}$ can be approximately 15 mm, which can correspond to implant sizes of 15 mm and 16 mm, respectively, which can be marked by graduation marks 24 and 25 (FIG. 1), respectively.

Other sounder heads may be included in the set having other sizes, such as a sounder head having sizing locations of 12 mm and 13 mm for implant sizes of 13 mm and 14 mm, respectively.

As discussed above, sizing locations can be selected based on the location along the scraping edge that corresponds to the size of an implant. The distance between sizing locations on each sounder head can be approximately 23 mm. Graduation marks 24 and 25 (FIG. 1) can be positioned along shank 14 at a distance from sizing locations $S_1$ and $S_2$ (FIG. 1) that it is anticipated to be the distance between where the sizing locations will impact cortical bone 58 and the proximal end of head 46 of bone 36 (FIG. 2B) when inserted into canal 38.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features may be grouped together to streamline the disclosure. This should not be interpreted as intending that an unclaimed disclosed feature is essential to any claim. Rather, inventive subject matter may lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

The claimed invention is:

1. A tool for performing an arthroplasty, the tool comprising:
    a shank extending along a central axis of the tool; and
    a sounder head comprising:
        a distal tip;
        a plurality of teeth extending proximally from the distal tip towards the shank, each tooth comprising:
            a distal cutting edge;
            a middle scraping edge;
            a proximal cutting edge;
            a radial tooth surface having:
                a distal panel disposed at the first positive rake angle;
                an intermediate panel disposed at the negative rake angle; and
                a proximal panel disposed at the second positive rake angle; and
            an outer tooth surface having:
                an arcuate distal segment;
                a tapered flat segment extending proximally from the arcuate distal segment; and
                a cylindrical flat segment extending proximally from the tapered flat segment; and
        a proximal portion connected to the shank;
    wherein each of the distal cutting edges has a first positive rake angle, each of the middle scraping edges has a negative rake angle, and each of the proximal cutting edges has a second positive rake angle;
    wherein rake angle is defined as an angle of a surface forming a cutting or scraping edge relative to a line extending radially from a centerline of the sounder head.

2. The tool of claim 1, wherein the shank includes graduation marks indicating sizes of the middle scraping edge, the sizes corresponding to diameters of the sounder head at distances from the graduation marks.

3. The tool of claim 1, wherein the second positive rake angle is greater than the first positive rake angle, wherein positive rake angles are defined as being positively advanced in a direction or rotation in which the plurality of teeth are configured to cut and scrape.

4. The tool of claim 1 wherein:
    the distal panel meets the arcuate distal segment to form the distal cutting edge;
    the intermediate panel meets the tapered flat segment to form the scraping edge; and the proximal panel meets the tapered flat segment to form the proximal cutting edge.

5. The tool of claim 1, wherein the sounder head includes a taper from the proximal cutting edge to the distal cutting edge.

6. The tool of claim 5, wherein the scraping edge includes the taper.

7. The tool of claim 5, wherein the taper is approximately 1.25 degrees relative to the central axis.

8. The tool of claim 1, wherein the proximal cutting edge has a larger diameter than the scraping edge and the distal cutting edge.

9. The tool of claim 1, wherein the sounder head further comprises a cylindrical section extending between the proximal portion and the proximal cutting edges.

10. A tool set for performing an arthroplasty, the tool set comprising:
a first tool comprising:
a first shank; and
a first cutting head, the first cutting head comprising:
a first distal tip; and
a plurality of edges extending proximally from the first distal tip towards the first shank, each edge comprising:
a first distal cutting edge;
a first middle scraping edge; and
a first proximal cutting edge;
a second tool comprising:
a second shank; and
a second cutting head, the second cutting head comprising:
a second distal tip; and
a plurality of edges extending proximally from the second distal tip towards the second shank, each edge comprising:
a second distal cutting edge;
a second middle scraping edge; and
a second proximal cutting edge;
a first implant having a diameter of the first cutting head; and
a second implant having a diameter of the second cutting head;
wherein the first diameter of the first cutting head is greater than the second diameter of the second cutting head.

11. The tool set of claim 10, wherein the first shank includes a graduation mark indicating the first diameter of the first cutting head at a location on the first shank a first distance from the first diameter, and the second shank includes a graduation mark indication the second diameter of the second cutting head at a location on the second shank a second distance from the second diameter.

12. The tool set of claim 10, wherein each of the first and second distal cutting edges has a first positive rake angle, each of the first and second middle scraping edges has a negative rake angle, and each of the first and second proximal cutting edges has a second positive rake angle, wherein rake angle is defined as an angle of a surface forming a cutting or scraping edge relative to a line extending radially from a centerline of the first or second cutting head.

13. The tool set of claim 10, wherein:
the first proximal cutting edge has a larger diameter than the first scraping edge and the first distal cutting edge; and
the second proximal cutting edge has a larger diameter than the second scraping edge and the second distal cutting edge.

14. A tool for performing an arthroplasty, the tool comprising:
a shank extending along a central axis of the tool; and
a sounder head comprising:
a distal tip;
a plurality of teeth extending proximally from the distal tip towards the shank, each tooth comprising:
a distal cutting edge;
a middle scraping edge; and
a proximal cutting edge; and
a proximal portion connected to the shank;
wherein the proximal cutting edge has a larger diameter than the scraping edge and the distal cutting edge;
wherein the shank includes graduation marks indicating sizes of the middle scraping edge, the sizes corresponding to diameters of the sounder head at distances from the graduation marks.

15. The tool of claim 14, wherein each of the distal cutting edges has a first positive rake angle, each of the middle scraping edges has a negative rake angle, and each of the proximal cutting edges has a second positive rake angle, wherein rake angle is defined as an angle of a surface forming a cutting or scraping edge relative to a line extending radially from a centerline of the sounder head.

16. The tool of claim 15, wherein the second positive rake angle is greater than the first positive rake angle.

17. The tool of claim 14, wherein:
the sounder head includes a taper from the proximal cutting edge to the distal cutting edge;
the scraping edge includes the taper; and
the taper is approximately 1.25 degrees relative to the central axis.

* * * * *